(12) United States Patent
Dwork

(10) Patent No.: US 8,926,692 B2
(45) Date of Patent: Jan. 6, 2015

(54) TRANSCATHETER PROSTHETIC HEART VALVE DELIVERY DEVICE WITH PARTIAL DEPLOYMENT AND RELEASE FEATURES AND METHODS

(75) Inventor: Joshua Dwork, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 669 days.

(21) Appl. No.: 12/757,088

(22) Filed: Apr. 9, 2010

(65) Prior Publication Data

US 2011/0251675 A1    Oct. 13, 2011

(51) Int. Cl.
*A61F 2/24*        (2006.01)
*A61F 2/966*       (2013.01)

(52) U.S. Cl.
CPC .............. *A61F 2/2418* (2013.01); *A61F 2/2436* (2013.01); *A61F 2002/9665* (2013.01)
USPC ......................................... 623/2.11; 623/1.11

(58) Field of Classification Search
USPC ......... 606/108, 191, 194, 198, 200; 623/1.11, 623/2.1, 2.11, 2.12
See application file for complete search history.

(56) References Cited

U.S. PATENT DOCUMENTS

| 5,397,306 | A  | * | 3/1995  | Nobuyoshi et al. | ...... 604/103.14 |
| 5,683,451 | A  |   | 11/1997 | Lenker et al. | |
| 5,824,041 | A  |   | 10/1998 | Lenker et al. | |
| 5,957,949 | A  |   | 9/1999  | Leonhardt et al. | |
| 8,414,645 | B2 | * | 4/2013  | Dwork et al. | ................. 623/2.11 |
| 2003/0199963 | A1 |   | 10/2003 | Tower et al. | |
| 2005/0090834 | A1 | * | 4/2005  | Chiang et al. | .................. 606/108 |
| 2005/0137688 | A1 |   | 6/2005  | Salahieh et al. | |
| 2005/0203614 | A1 | * | 9/2005  | Forster et al. | ................. 623/2.11 |
| 2005/0222604 | A1 | * | 10/2005 | Schaeffer | ...................... 606/200 |
| 2006/0004439 | A1 |   | 1/2006  | Spenser et al. | |
| 2006/0052867 | A1 |   | 3/2006  | Revuelta et al. | |
| 2006/0259136 | A1 |   | 11/2006 | Nguyen et al. | |
| 2006/0265056 | A1 |   | 11/2006 | Nguyen et al. | |
| 2007/0005131 | A1 |   | 1/2007  | Taylor | |
| 2007/0088431 | A1 |   | 4/2007  | Bourang et al. | |
| 2007/0239266 | A1 |   | 10/2007 | Birdsall | |
| 2007/0239269 | A1 |   | 10/2007 | Dolan et al. | |
| 2007/0270932 | A1 | * | 11/2007 | Headley et al. | ............. 623/1.11 |
| 2008/0065011 | A1 |   | 3/2008  | Marchand et al. | |
| 2008/0071367 | A1 | * | 3/2008  | Bergin et al. | ................. 623/2.11 |

(Continued)

FOREIGN PATENT DOCUMENTS

| GB | 2433700    | 7/2007  |
| WO | 2008/138584 | 11/2008 |

(Continued)

*Primary Examiner* — Katherine M Shi

(57) ABSTRACT

A delivery device for percutaneously deploying a stented prosthetic heart valve, including a delivery sheath, an inner shaft, and a spindle. The inner shaft is slidably disposed within a lumen of the delivery sheath. The spindle is attached to the shaft and includes a hub defining at least one longitudinal slot sized to slidably receive a post of the stented valve. An outer surface of the hub forms a curved proximal segment. The device provides a loaded state in which the delivery sheath retains the stented valve over the inner shaft and coupled to the spindle via the slot. In a deployed state, the distal end of the delivery sheath is withdrawn from the prosthesis to permit the stented valve to release from the slot, sliding along the curved outer surface of the hub.

30 Claims, 14 Drawing Sheets

(56) References Cited

U.S. PATENT DOCUMENTS

| | | |
|---|---|---|
| 2008/0188928 A1 | 8/2008 | Salahieh et al. |
| 2008/0234797 A1 | 9/2008 | Styrc |
| 2008/0255651 A1 | 10/2008 | Dwork |
| 2008/0264102 A1* | 10/2008 | Berra .................. 63/1.11 |
| 2009/0093876 A1 | 4/2009 | Nitzan et al. |
| 2009/0171447 A1 | 7/2009 | von Segesser et al. |
| 2010/0049313 A1* | 2/2010 | Alon et al. ................ 623/2.11 |
| 2010/0217382 A1* | 8/2010 | Chau et al. ................ 623/1.26 |

FOREIGN PATENT DOCUMENTS

| | | |
|---|---|---|
| WO | 2009/024859 | 2/2009 |
| WO | 2009/053497 | 4/2009 |
| WO | 2009/091509 | 7/2009 |

\* cited by examiner

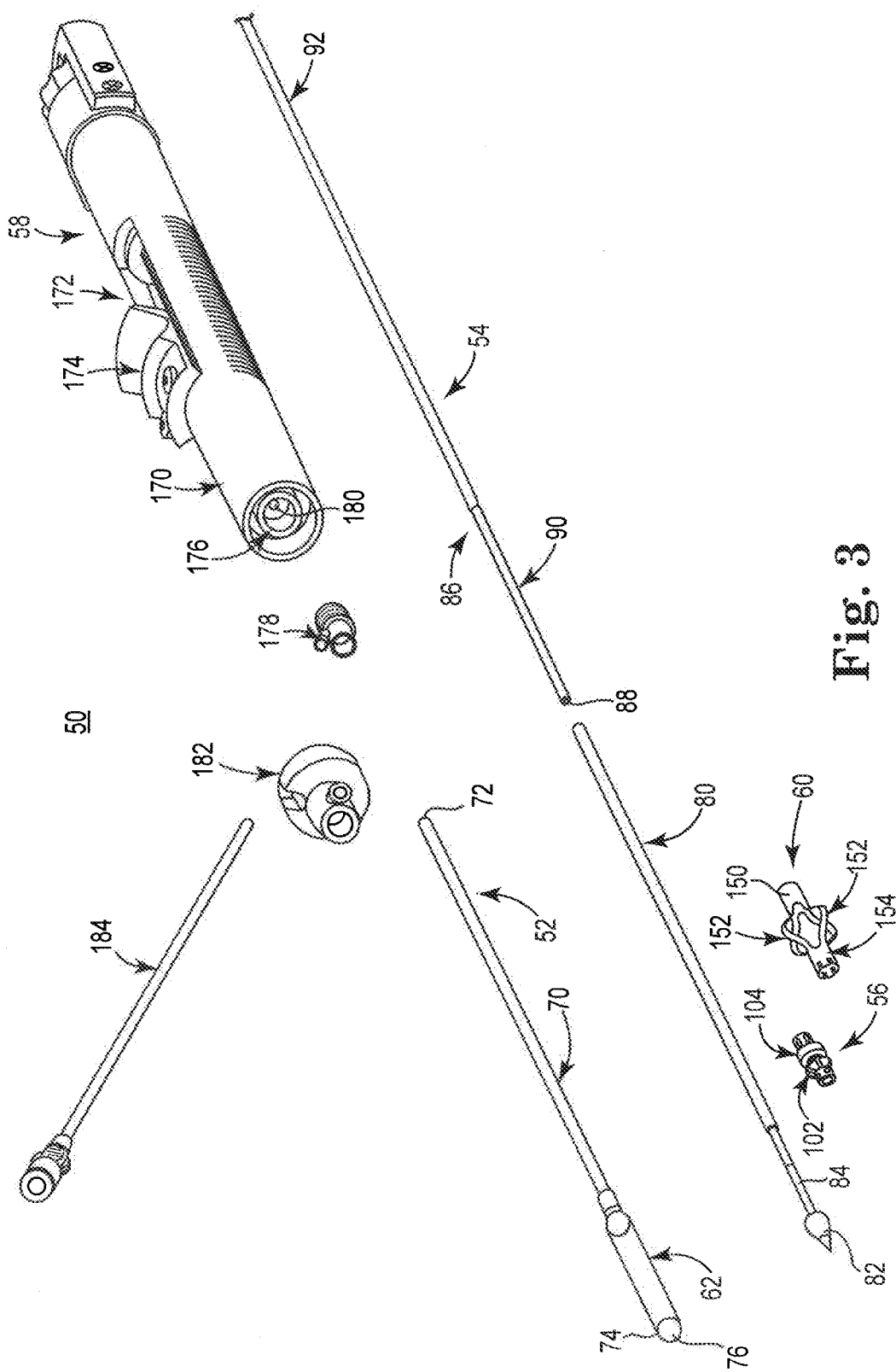

TRANSCATHETER PROSTHETIC HEART VALVE DELIVERY DEVICE WITH PARTIAL DEPLOYMENT AND RELEASE FEATURES AND METHODS

BACKGROUND

The present disclosure relates to systems, devices, and methods for percutaneous implantation of a prosthetic heart valve. More particularly, it relates to delivery systems, devices, and methods for transcatheter implantation of a stented prosthetic heart valve.

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be repaired (e.g., the aortic valve annulus). Although transcatheter techniques have attained widespread acceptance with respect to the delivery of conventional stents to restore vessel patency, only mixed results have been realized with percutaneous delivery of the more complex prosthetic heart valve.

Various types and configurations of prosthetic heart valves are available for percutaneous valve replacement procedures, and continue to be refined. The actual shape and configuration of any particular transcatheter prosthetic heart valve is dependent to some extent upon the native shape and size of the valve being repaired (i.e., mitral valve, tricuspid valve, aortic valve, or pulmonary valve). In general, prosthetic heart valve designs attempt to replicate the functions of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). For many percutaneous delivery and implantation devices, the stent frame of the valved stent is made of a self-expanding material and construction. With these devices, the valved stent is crimped down to a desired size and held in that compressed arrangement within an outer delivery sheath, for example. Retracting the sheath from the valved stent allows the stent to self-expand to a larger diameter, such as when the valved stent is in a desired position within a patient. In other percutaneous implantation devices, the valved stent can be initially provided in an expanded or uncrimped condition, then crimped or compressed on a balloon portion of catheter until it is as close to the diameter of the catheter as possible. The so-loaded balloon catheter is slidably disposed within an outer delivery sheath. Once delivered to the implantation site, the balloon is inflated to deploy the prosthesis. With either of these types of percutaneous stented prosthetic valve delivery devices, conventional sewing of the prosthetic heart valve to the patient's native tissue is typically not necessary.

It is imperative that the stented prosthetic heart valve be accurately located relative to the native annulus immediately prior to full deployment from the catheter as successful implantation requires the prosthetic heart valve intimately lodge and seal against the native annulus. If the prosthesis is incorrectly positioned relative to the native annulus, serious complications can result as the deployed device can leak and may even dislodge from the native valve implantation site. As a point of reference, this same concern does not arise in the context of other vascular stents; with these procedures, if the target site is "missed," another stent is simply deployed to "make-up" the difference.

To carefully and safely deploy a transcatheter prosthetic heart valve, a clinician can employ imaging technology to evaluate the location of the prosthesis immediately prior to deployment. In particular, one desirable transcatheter prosthetic heart valve implantation technique entails partially deploying a distal region of the prosthesis from the delivery device and then evaluating a position of the deployed distal region relative to the native annulus. The clinician may further desire the ability to resheath or recapture the partially deployed region for subsequent repositioning of the prosthesis. Regardless, in the partially deployed state, the proximal region of the prosthetic heart valve must remain coupled to the delivery device. While, in theory, retaining a partially deployed prosthetic heart valve to the delivery device is straightforward, in actual practice the constraints presented by the stented prosthetic heart valve render the technique exceedingly difficult. In particular, the delivery device must not only securely retain the prosthetic heart valve in the partially deployed state, but also must consistently operate to release the prosthetic heart valve when full deployment is desired.

A stented heart valve is purposefully designed to rigidly resist collapsing forces once deployed so as to properly anchor itself in the anatomy of the heart. Thus, the delivery device component (e.g., outer delivery sheath) employed to retain the prosthesis in a collapsed arrangement must be capable of exerting a significant radial force. Conversely, the component cannot be overly rigid so as to avoid damaging the transcatheter heart valve during deployment. Along these same lines, the aortic arch must be traversed with many percutaneous heart valve replacement procedures, necessitating that the delivery device provide sufficient articulation attributes. To meet these constraints, the outer delivery sheath typically incorporates a circumferentially rigid capsule, and a coupling structure is disposed within the delivery sheath for temporarily capturing the stented valve. While viable, conventional delivery device designs robustly engage the prosthetic heart valve within the capsule; this robust engagement facilitates the partial deployment technique described above, but the prosthetic heart valve may undesirably catch on the inner engagement structure when full deployment is intended and/or numerous, complex components are required to ensure complete deployment. Further, clinicians prefer that a significant portion of the prosthetic heart valve be exposed/expanded in the partially deployed state (e.g., the inflow region and at least a portion of the outflow region of the prosthesis). Unfortunately, existing delivery system designs cannot consistently meet this need.

In light of the above, a need exists for heart valve repair systems and corresponding stented transcatheter prosthetic heart valve delivery devices and methods that satisfy the constraints associated with percutaneous heart valve implantation and permit consistent partial and full deployment of the prosthesis.

SUMMARY

Some aspects in accordance with principles of the present disclosure relate to a delivery device for percutaneously deploying a stented prosthetic heart valve. The prosthetic heart valve has a stent frame to which a valve structure is attached. The delivery device includes a delivery sheath assembly, an inner shaft, and a spindle. The delivery sheath assembly terminates at a distal end and defines a lumen. The inner shaft is slidably disposed within the lumen. The spindle is attached to the shaft and includes a tubular base and a hub. The hub projects radially outwardly relative to the base, and defines at least one longitudinal slot sized to slidably receive a corresponding post component of the prosthetic heart valve stent frame. Further, an outer surface of the hub forms a proximal segment and a distal segment, with the proximal segment being curved in extension toward the distal segment. With this in mind, the device is configured to provide a loaded state in which the delivery sheath assembly retains the stented prosthetic heart valve over the inner shaft and coupled to the spindle via the at least one longitudinal slot. The device is further configured to provide a deployed state in which the distal end of the delivery sheath assembly is withdrawn from the prosthetic heart valve to permit the prosthetic heart valve to release from the longitudinal slot. In some embodiments, the hub forms a plurality of circumferentially spaced longitudinal slots. In other embodiments, the outer surface, as collectively defined by proximal and distal segments, approximates a semi-circle. In yet other embodiments, the delivery device further includes a release sheath assembly disposed between the delivery sheath assembly and the spindle in the loaded state, the release sheath assembly including a release sheath slidably received over the proximal segment of the hub. In related embodiments, the release sheath forms a plurality of circumferentially spaced notches at a leading end thereof, with the notches being longitudinally aligned with respective ones of the slots in the hub.

Yet other aspects in accordance with principles of the present disclosure relate to a system for repairing a defective heart valve of a patient. The system includes a prosthetic heart valve and a delivery device. The prosthetic heart valve has a stent frame and a valve structure attached to the stent frame. Further, the stent frame includes a proximal region forming at least one post. The delivery device includes a delivery sheath assembly, an inner shaft, and a spindle. The delivery sheath assembly terminates at a distal end and defines a lumen. The inner shaft is slidably disposed within the lumen. The spindle is attached to the inner shaft and includes a tubular base and a hub. The hub projects radially outwardly relative to the base and defines at least one longitudinal slot sized to slidably receive the post of the stent frame. Further, an outer surface of the hub forms a proximal segment and a distal segment, with the proximal segment being curved in extension toward the distal segment. With this construction, the system is configured to provide a loaded condition in which the prosthetic heart valve is retained between the delivery sheath assembly and the inner shaft, including the post being slidably captured within the longitudinal slot. In some embodiments, the post has a T-like shape. In other embodiments, the proximal region of the stent frame forms a plurality of the posts, with the hub forming a corresponding number of longitudinal slots. In other constructions, a deployment condition of the system includes the stent frame self-expanding from the delivery device, with the post sliding along the curved proximal segment of the hub outer surface.

Yet other aspects in accordance with principles of the present disclosure relate to a method of percutaneously deploying a stented prosthetic heart valve to an implantation site of a patient. The method includes receiving a delivery device loaded with a radially expandable prosthetic heart valve having a stent frame to which a valve structure is attached. The delivery device includes a delivery sheath assembly containing the prosthetic heart valve in a compressed arrangement over an inner shaft in a loaded state of the device, as well as a spindle attached to the shaft. The spindle includes a tubular base and a hub projecting radially outwardly relative to the base and defining at least one longitudinal slot within which a post of the stent frame is slidably received in the loaded state. Further, an outer surface of the hub includes a curved proximal segment. The prosthetic heart valve is delivered in the compressed arrangement through a bodily lumen of the patient and to the implantation site via the delivery device in the loaded state. The delivery sheath assembly is proximally retracted from the prosthetic heart valve. The post is permitted to release from the slot, including a surface of the post sliding along the curved proximal segment of the hub's outer surface such that the prosthetic heart valve deploys from the delivery device. In some embodiments, the delivery device further includes a release sheath slidably coupled over the proximal segment of the hub in the loaded state to capture the post relative to the spindle, with the release sheath forming a notch that is longitudinally aligned with the slot and being proximally retractable with proximal retraction of the delivery sheath assembly. With these embodiments, the method can further include proximally retracting the release sheath relative to the hub, with the post self-pivoting relative to the spindle, including a portion of the post passing through the slot and the corresponding notch.

BRIEF DESCRIPTION OF THE DRAWINGS

FIG. 3 is an exploded, perspective view of a stented prosthetic heart valve delivery device in accordance with principles of the present disclosure;

DETAILED DESCRIPTION

Figure 1A:
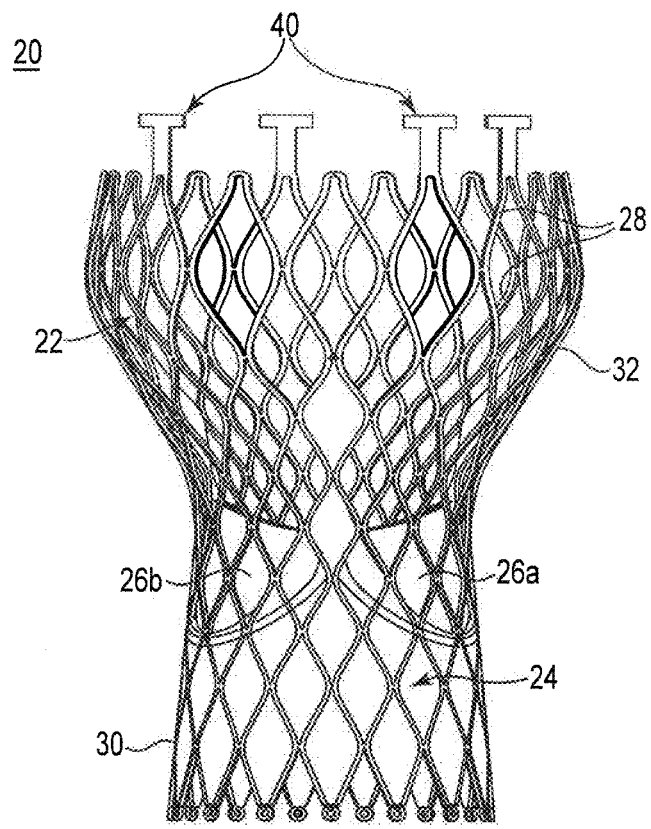
FIG. 1A is a side view of a stented prosthetic heart valve useful with systems and methods of the present disclosure and in a normal, expanded arrangement.

As referred to herein, stented transcatheter prosthetic heart valves useful with and/or as part of the various systems, devices, and methods of the present disclosure may assume a wide variety of different configurations, such as a bioprosthetic heart valve having tissue leaflets or a synthetic heart valve having polymeric, metallic, or tissue-engineered leaflets, and can be specifically configured for replacing any heart valve. Thus, the stented prosthetic heart valve useful with the systems, devices, and methods of the present disclosure can be generally used for replacement of a native aortic, mitral, pulmonic, or tricuspid valve, for use as a venous valve, or to replace a failed bioprosthesis, such as in the area of an aortic valve or mitral valve, for example.

In general terms, the stented prosthetic heart valves of the present disclosure include a stent or stent frame maintaining a valve structure (tissue or synthetic), with the stent having a normal, expanded arrangement and collapsible to a compressed arrangement for loading within a delivery device. The stent is normally constructed to self-deploy or self-expand when released from the delivery device. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems, devices, and methods of the present disclosure are described in U.S. Publication Nos. 2006/0265056; 2007/0239266; and 2007/0239269, the teachings of each which are incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a variety of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine paracardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two (typically three) leaflets; however, replacement prosthetic heart valves of the types described herein can incorporate more or less than three leaflets.

Some embodiments of the stent frames can be a series of wires or wire segments arranged such that they are capable of self-transitioning from a compressed or collapsed arrangement to the normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the normal, expanded arrangement. In the compressed arrangement, such a stent frame support structure with attached valves can be mounted onto a delivery device. The stent frame support structures are configured so that they can be changed to their normal, expanded arrangement when desired, such as by the relative movement of one or more sheaths relative to a length of the stent frame.

The wires of these stent frame support structures in embodiments of the present disclosure can be formed from a shape memory material such as a nickel titanium alloy (e.g., Nitinol™) With this material, the support structure is self-expandable from the compressed arrangement to the normal, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery device that can be used includes a catheter with a retractable sheath that covers the stent frame until it is to be deployed, at which point the sheath can be retracted to allow the stent frame to self-expand. Further details of such embodiments are discussed below.

Figure 1B:
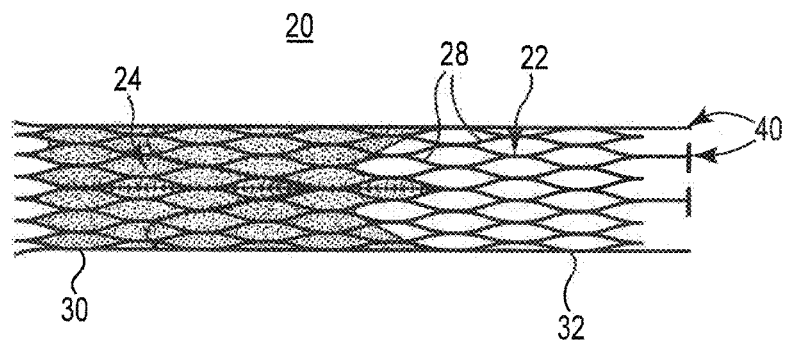
FIG. 1B is a side view of the prosthetic heart valve of FIG. 1A in a compressed arrangement.

With the above understanding in mind, one non-limiting example of a stented prosthetic heart valve 20 useful with systems and methods of the present disclosure is illustrated in FIG. 1A. As a point of reference, the prosthetic heart valve 20 is shown in a normal or expanded arrangement in the view of FIG. 1A; FIG. 1B illustrates the prosthetic heart valve 20 in a compressed arrangement (e.g., when compressively retained within an outer catheter or sheath). The prosthetic heart valve 20 includes a stent or stent frame 22 and a valve structure 24. The stent frame 22 can assume any of the forms described above, and is generally constructed so as to be self-expandable from the compressed arrangement (FIG. 1B) to the normal, expanded arrangement (FIG. 1A). In other embodiments, the stent frame 22 is expandable to the expanded arrangement by a separate device (e.g., a balloon internally located within the stent frame 22). The valve structure 24 is assembled to the stent frame 22 and provides two or more (typically three) leaflets 26a, 26b. The valve structure 24 can assume any of the forms described above, and can be assembled to the stent frame 22 in various manners, such as by sewing the valve structure 24 to one or more of the wire segments 28 defined by the stent frame 22.

With the but one acceptable construction of FIGS. 1A and 1B, the prosthetic heart valve 20 is configured for repairing an aortic valve. Alternatively, other shapes are also envisioned, adapted for the specific anatomy of the valve to be repaired (e.g., stented prosthetic heart valves in accordance with the present disclosure can alternatively be shaped and/or sized for replacing a native mitral, pulmonic, or tricuspid valve). Regardless, the valve structure 24 can be arranged to extend less than an entire length of the stent frame 22. In particular, the valve structure 24 can be assembled to, and extend along, an inflow region 30 of the prosthetic heart valve 20, whereas an outflow region 32 is free of the valve structure 24 material. The terms "inflow" and "outflow" are in reference to an arrangement of the prosthetic heart valve 20 upon final implantation relative to the native aortic valve (or other valve) being repaired. A wide variety of other constructions are also acceptable and within the scope of the present disclosure. For example, the valve structure 24 can be sized and shaped to extend along an entirety, or a near entirety, of a length of the stent frame 22. With embodiments in which the prosthetic heart valve 20 is to be implanted via a retrograde approach, the prosthetic heart valve 20 will be arranged within the corresponding delivery device such that the inflow region 30 is distal the outflow region 32. Thus, the inflow region 30 can alternatively be referenced as the distal region of the prosthetic heart valve 20, whereas the outflow region 32 serves as the proximal region. With these conventions in mind, a proximal end 36 of the stent frame 22 forms, in some embodiments, a plurality of posts 40. The posts 40 are defined at an intersection of two (or more) adjacent ones of the wire segments 28, and are circumferentially spaced about a circumference defined by the stent frame 22. While the stent frame 22 is shown in FIGS. 1A and 1B as having four of the posts 40, any other number, either greater or lesser, is equally acceptable. For example, the stent frame 22 can include as few as a single one of the posts 40.

Figure 2:
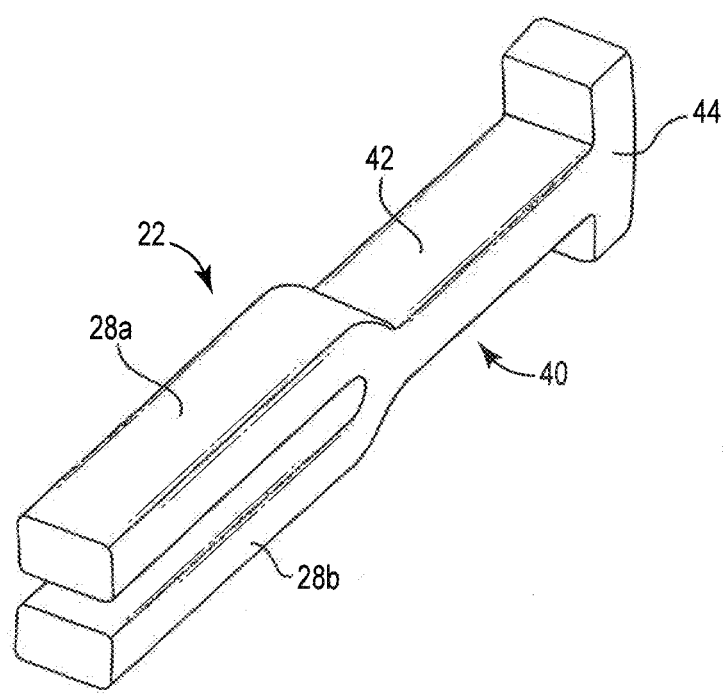
FIG. 2 is an enlarged, perspective view of a post portion of the prosthetic heart valve of FIGS. 1A and 1B.

The posts 40 can assume various forms, and in some embodiments are identical. FIG. 2 illustrates one construction of the post 40 contemplated by the present disclosure in greater detail. As a point of reference, in the view of FIG. 2, two of the wire segments 28a, 28b are illustrated as intersecting at the post 40, with the post 40 projecting proximally from the wire segments 28a, 28b; a remainder of the stent frame 22 is omitted from the view for ease of explanation. The post 40 includes a shoulder 42 and a head 44. With respect to an orientation of the post 40 relative to the circumference defined by the stent frame 22 (FIG. 1A), the shoulder 42 and the head 44 can be described as having or defining a circumferential width, with the circumferential width of the head 44 being greater than that of the shoulder 42 for reasons made clear below. With some constructions, then, the post 40 can have a T-like shape. These and other features of the post 40, as well as the stent frame 22 as a whole, are described below in the context of loading to, and releasing from, a delivery device.

With the above understanding of the prosthetic heart valve 20 in mind, one embodiment of a transcatheter stented prosthetic heart valve delivery device 50 in accordance with principles of the present disclosure is shown in FIG. 3. The delivery system 50 includes a delivery sheath assembly 52, an inner shaft assembly 54, a retention body or spindle 56, and a handle 58. Other optional components, such as a release sheath assembly 60, can also be included. Details on the various components are provided below. In general terms, however, the delivery device 50 combines with a stented prosthetic heart valve (not shown) to form a system for repairing a defective heart valve of a patient. The delivery device 50 provides the loaded state in which a stented prosthetic heart valve is coupled to the inner shaft assembly 54 via the spindle 56, and compressively retained within a capsule 62 of the delivery sheath assembly 52. The delivery sheath assembly 52 can be manipulated to withdraw the capsule 62 proximally from the prosthetic heart valve via operation of the handle 58, permitting the prosthesis to self-expand and release from the inner shaft assembly 54. The optional release sheath assembly 60, where provided, can operate to effectuate this release. Further, the handle 58 can be operated to maneuver the capsule 62 to effectuate a partial deployment state in which a distal region of the prosthetic heart valve is permitted to self-expand, whereas a proximal region of the prosthesis remains coupled to the spindle 56.

Various features of the components 52-60 reflected in FIG. 3 and described below can be modified or replaced with differing structures and/or mechanisms. Thus, the present disclosure is in no way limited to the delivery sheath assembly 52, the inner shaft assembly 54, the handle 58, etc., as shown and described below. For example, apart from the spindle 56, the delivery device 50 can have any of the constructions described in U.S. Provisional application Ser. No. 61/237,373 filed Aug. 27, 2009 and entitled "Transcatheter Valve Delivery Systems and Methods"; the teachings of which are incorporated herein by reference. More generally, delivery devices in accordance with the present disclosure provide features capable of compressively retaining a self-deploying, stented prosthetic heart valve (e.g., the capsule 62 in combination with the spindle 56), and a mechanism capable of effectuating partial and full release or deployment of the prosthesis (e.g., retracting the capsule 62 alone or in combination with the optional release sheath assembly 60).

In some embodiments, the delivery sheath assembly 52 includes the capsule 62 and a shaft 70, and defines proximal and distal ends 72, 74. A lumen 76 is formed by the delivery sheath assembly 52, extending from the distal end 74 through the capsule 62 and at least a portion of the shaft 70. The lumen 76 can be open at the proximal end 72. The capsule 62 extends distally from the shaft 70, and in some embodiments has a more stiffened construction (as compared to a stiffness of the shaft 70) that exhibits sufficient radial or circumferential rigidity to overtly resist the expected expansive forces of the stented prosthetic heart valve (not shown) when compressed within the capsule 62. For example, the shaft 70 can be a polymer tube embedded with a metal braiding, whereas the capsule 62 includes a laser-cut metal tube that is optionally embedded within a polymer covering. Alternatively, the capsule 62 and the shaft 70 can have a more uniform construction (e.g., a continuous polymer tube). Regardless, the capsule 62 is constructed to compressively retain the stented prosthetic heart valve at a predetermined diameter when loaded within the capsule 62, and the shaft 70 serves to connect the capsule 62 with the handle 58. The shaft 70 (as well as the capsule 62) is constructed to be sufficiently flexible for passage through a patient's vasculature, yet exhibits sufficient longitudinal rigidity to effectuate desired axial movement of the capsule 62. In other words, proximal refraction of the shaft 70 is directly transferred to the capsule 62 and causes a corresponding proximal refraction of the capsule 62. In other embodiments, the shaft 70 is further configured to transmit a rotational force or movement onto the capsule 62.

The inner shaft assembly 54 can have various constructions appropriate for supporting a stented prosthetic heart valve within the capsule 62. In some embodiments, the inner shaft assembly 54 include an inner support shaft 80 and a tip 82. The inner support shaft 80 is sized to be slidably received within the lumen 76 of the delivery sheath assembly 52, and is configured for mounting of the spindle 56 and the optional release sheath assembly 60. The inner support shaft 80 can include a distal segment 84 and a proximal segment 86. The distal segment 84 connects the tip 82 to the proximal segment 86, with the proximal segment 86, in turn, coupling the inner shaft assembly 54 with the handle 58. The components 80-86 can combine to define a continuous lumen 88 (referenced generally) sized to slidably receive an auxiliary component such as a guide wire (not shown).

The distal segment 84 can be a flexible polymer tube embedded with a metal braid. Other constructions are also acceptable so long as the distal segment 84 exhibits sufficient structural integrity to support a loaded, compressed stented prosthetic heart valve (not shown), as well as the spindle 56 and the optional release sheath assembly 60 mounted thereto. The proximal segment 86 can include, in some constructions, a leading portion 90 and a trailing portion 92. The leading portion 90 serves as a transition between the distal and proximal segments 84, 86, and thus in some embodiments is a flexible polymer tubing (e.g., PEEK) having an outer diameter slightly less than that of the distal segment 84. The trailing portion 92 has a more rigid construction (e.g., a metal hypotube), adapted for robust assembly with the handle 58. Other materials and constructions are also envisioned. For example, in alternative embodiments, the distal and proximal segments 84, 86 are integrally formed as a single, homogenous tube or solid shaft.

The tip 82 forms or defines a nose cone having a distally tapering outer surface adapted to promote atraumatic contact with bodily tissue. The tip 82 can be fixed or slidable relative to the inner support shaft 80.

Figure 4A:
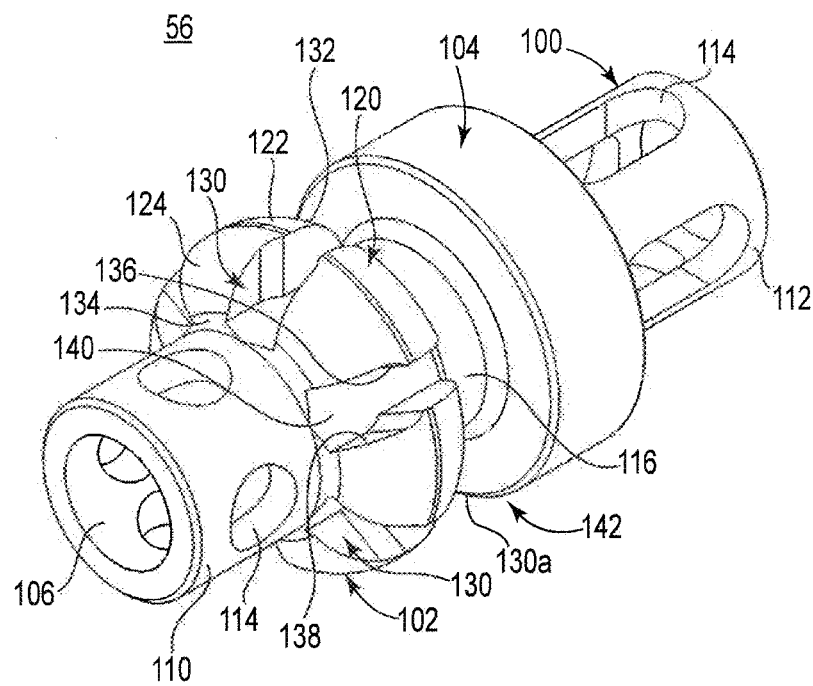
FIG. 4A is an enlarged, perspective view of a spindle portion of the delivery device of FIG. 3.

The spindle 56 serves to selectively couple corresponding features of the stented prosthetic heart valve (not shown) relative to the inner shaft assembly 54, and can be configured for assembly over the inner support shaft 80. One embodiment of the spindle 56 is shown in greater detail in FIGS. 4A and 4B.

The spindle 56 includes a tubular base 100, a hub 102, and a flange 104. The hub 102 and the flange 104 radially project from the tubular base 100, with the hub 102 forming various features configured to selectively engage the post(s) 40 (FIG. 2) of the stented prosthetic heart valve 20 (FIG. 1A) as described below.

The tubular base 100 is configured to facilitate mounting of the spindle 56 over the inner support shaft 80 (FIG. 3), and thus can define a central passageway or lumen 106 sized to receive the corresponding section of the inner support shaft 80. In this regard, the base 100 can include leading and trailing sections 110, 112 each forming one or more apertures 114 that facilitate attachment of the spindle 56 to the inner support shaft 80 (e.g., via an adhesive applied in the apertures 114). Other mounting techniques are also envisioned such that one or both of the leading sections 110, 112 can be omitted. Regardless, an intermediate section 116 is formed or defined between the hub 102 and the flange 104.

Figure 4B:
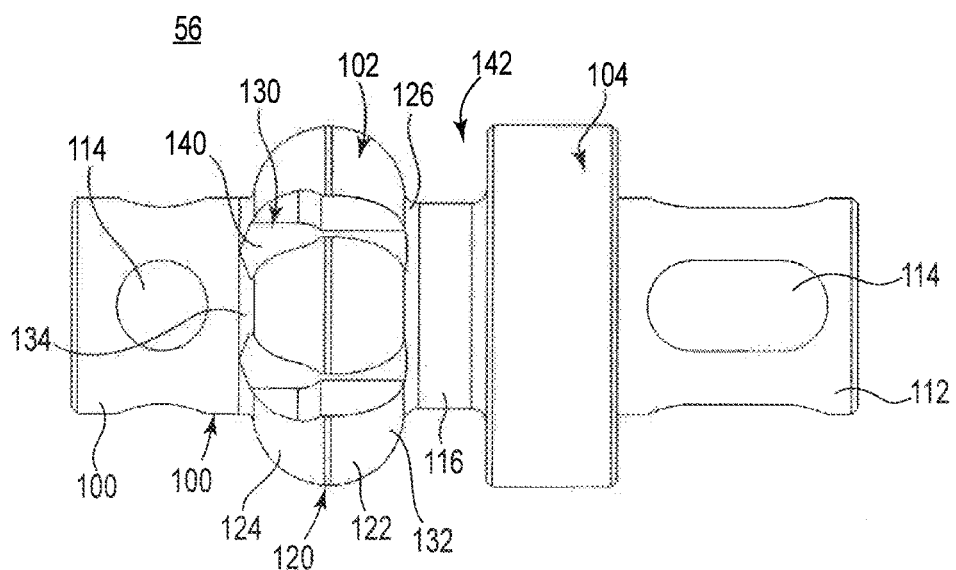
FIG. 4B is a side view of the spindle of FIG. 4A.

The hub 102 projects radially outwardly from the tubular base 100 to define an outer surface 120. Relative to an orientation of the spindle 56 upon final construction of the delivery device 50 (FIG. 3), the outer surface 120 can be viewed as having or defining a proximal segment 122 and a distal segment 124. The proximal segment 122 of the outer surface 120 is curved, for example defining a convex curve in distal extension toward the distal segment 124. As best shown in FIG. 4B, the proximal segment 122 of the outer surface 120 can optionally form a ramp-like face 126 immediately adjacent the intermediate section 116 such that the proximal segment 122 has a curvilinear shape. However, at least a majority of the proximal segment 122 is a smooth curve. The distal segment 124 of the outer surface 120 can also define a convex curvature, with the segments 122, 124 combining to approximate a semi-circle. Alternatively, the distal segment 124 of the outer surface 120 can have a variety of differing shapes that may or may not be curved. As described in greater detail below, however, the curved shape of the proximal segment 122 of the outer surface 120 is free of edges or corners and facilitates consistent deployment of the prosthetic heart valve 20 (FIG. 1A) when desired.

In addition to the curved proximal segment 122 of the outer surface 120, the hub 102 forms or defines at least one longitudinal slot 130. In some embodiments, a plurality of the longitudinal slots 130 are formed in the hub 102, commensurate with the number of the posts 40 (FIG. 1A) provided with the prosthetic heart valve 20 (FIG. 1A). In related embodiments, the plurality of longitudinal slots 130 can be identical and are equidistantly spaced relative to a circumference of the hub 102. Alternatively, only a single one of the slots 130 need be provided. The slot(s) 130 extends through a longitudinal thickness of the hub 102, and is open at the proximal and distal faces 132, 134 of the hub 102. For example, with respect to the first slot 130a identified in FIG. 4A, the slot 130a is defined by opposing side walls 136, 138 and a floor 140. The side walls 136, 138 define a height of the slot 130a, with a maximum height of the slot 130a being commensurate with (e.g., slightly greater than) a thickness of the stent frame post 40 (FIG. 2). The side walls 136, 138 are relatively smooth to facilitate sliding of the post 40 relative thereto; similarly, the floor 140 is substantially flat so as to provide a smooth surface against which the post 40 can reside. A circumferential width of the slot 130a corresponds with a circumferential width of the post shoulder 42 (FIG. 2). In some constructions, the circumferential width of the slot 130a can be slightly enlarged at the distal face 134 as compared to the circumferential width of the slot 130a at the proximal face 132 to more easily accommodate loading of the prosthetic heart valve 20. Regardless, the circumferential width of the slot 130a at the proximal face 132 is less than the circumferential width of the post head 44 (FIG. 2).

The flange 104 is proximally spaced from the hub 102, and radially projects from the tubular base 100. With this spacing, then, the intermediate section 116 of the tubular base 100 provides a reduced diameter cylindrical surface interposed between the hub 102 and the flange 104, with a diameter of the intermediate section 116 approximating, or longitudinally aligned with, the floor 140 of each of the longitudinal slots 130. The larger diameter flange 104 combines with the hub 102 and the intermediate section 116 to create a trough 142 configured to selectively receive the post head 44 (FIG. 2) as described below. The outer diameter of the flange 104 can approximate a maximum outer diameter of the hub 102 for reasons made clear below. In other embodiments, however the flange 104 can be omitted.

The spindle 56 can be integrally formed as a homogenous part in some embodiments. In other constructions, one or more of the hub 102 and the flange 104 can be separately manufactured and subsequently assembled to the tubular base 100. Alternatively, the hub 102 and/or the flange 104 can be directly mounted onto the inner support shaft 80. Regardless, the spindle 56 is constructed of a relatively rigid material, able to maintain a structural integrity of the spindle 56 in supporting the prosthetic heart valve 20 in the compressed arrangement.

Returning to FIG. 3, the optional release sheath assembly 60 is generally constructed to selectively capture the prosthetic heart valve 20 (FIG. 1A) to the spindle 56, and in particular the hub 102. With this in mind, the release sheath assembly 60 includes a mounting collar 150, one or more biasing members 152, and a release sheath 154. In general terms, the mounting collar 150 couples the release sheath assembly 60 to the inner support shaft 80. The release sheath 154 is sized to be slidably disposed over the spindle 56, with the biasing members 152 serving to bias the release sheath 154 to a longitudinal position relative to the coupling body 150, and thus relative to the spindle 56, as described below.

The mounting collar 150 can assume various configurations appropriate for non-moveable, fixed mounting to the inner support shaft 80. For example, the mounting collar 150 can be a ring that is bonded to the inner support shaft 80. Other structures appropriate for establishing a fixed location relative to the inner support shaft 80 as well as resisting forces generated in or by the biasing member(s) 152 are also envisioned. For example, in other embodiments, the mounting collar 150 can be omitted and an end of each of the biasing member(s) 152 opposite the release sheath 154 directly attached to the inner support shaft 80.

The biasing members 152 are leaf spring-like bodies, and are spaced from one another about a periphery of the release sheath 154. In some constructions, the release sheath assembly 60 will include at least two of the biasing members 152, which may be positioned at generally opposite sides of the release sheath 154, if desired, although it is possible that they are positioned different relative to each other. In other constructions, only one of the biasing members 152 is provided. In yet other embodiments, the release sheath assembly 60 includes three or more biasing members 152, and each of the biasing members 152 may be configured the same or differently than the other biasing members 152. Regardless, and as described in greater detail below, the biasing member(s) 152 can have a shape memory attribute, normally or naturally assuming the outwardly curved shape reflected in FIG. 3, and can be externally forced to deflect to a more straightened shape. Upon removal of the external force, the biasing member(s) 152 self-revert back toward the normal curved shape. Other spring-related shapes or structures are also acceptable.

Figure 5:
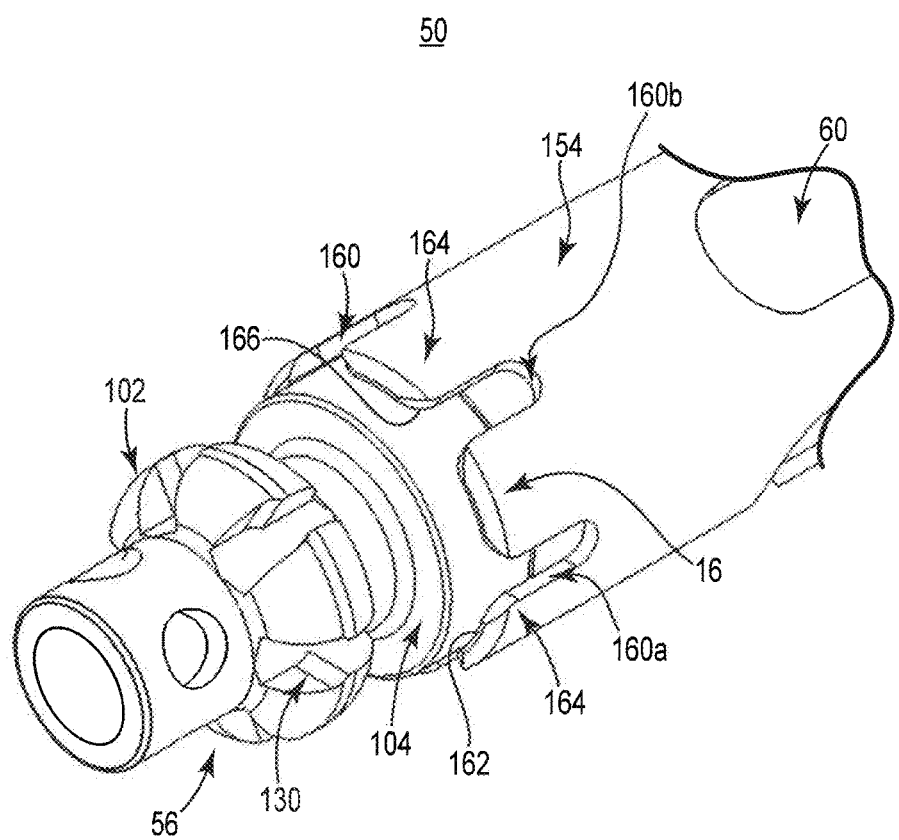
FIG. 5 is a perspective view of a portion of a release sheath assembly component of the delivery device of FIG. 3.

The release sheath 154 is a tubular body sized to be slidably received over the spindle 56, and in particular the hub 102 and the flange 104. The release sheath 154 is designed to move freely over the hub 102 and the flange 104 due to a gap clearance (e.g., on the order of 0.001 inch or greater) that is provided between the release sheath 154 and the maximum outer diameter of the hub 102 and the flange 104. In some constructions, and as best shown in FIG. 5 (that otherwise illustrates the release sheath 154 assembled over the flange 104 of the spindle 56), the release sheath 154 forms or defines at least one longitudinal notch 160 extending from, and open relative to, a distal end 162 thereof. The release sheath 154 normally includes a plurality of the notches 160 corresponding with the number of the longitudinal slots 130 provided with the hub 102. The notches 160 can be identical and are arranged relative to a circumference of the release sheath 154 such that each of the notches 160 is longitudinally aligned with a corresponding one of the slots 130 upon assembly of the release sheath 154 over the flange 104. With embodiments in which the release sheath 154 forms two (or more) of the notches 160, two (or more) fingers 164 are formed by or between adjacent ones of the notches 160. For example, a first finger 164a is defined between the first and second notches 160a, 160b. While each of the notches 160 can have a relatively uniform circumferential width, an increased circumferential width can be defined immediately adjacent the distal end 162. That is to say, for reasons made clear below, a distal zone 166 of each of the notches 160 can have an increased or distally increasing circumferential width as compared to a remainder of the notch 160 such that at the distal end 162, the notch 160 is enlarged. Alternatively, the notches 160 can have other shapes, and in yet other embodiments are omitted.

Returning to FIG. 3, the release sheath assembly 60, including the biasing members 152 and/or the release sheath 154, can be made of one of more materials such as metal or polymers (e.g., Nitinol™, stainless steel, Delrin™, and the like). The material(s) have a thickness on the order of 0.002-0.007 inch, for example, although the thickness can be lower or higher than this size range. The release sheath assembly 60 can have a length on the order of 5-15 mm, for example, in order to provide both flexibility and spring-radial strength to the components. The material(s) can have either a closed cell or an open-cell design.

Figure 6A:
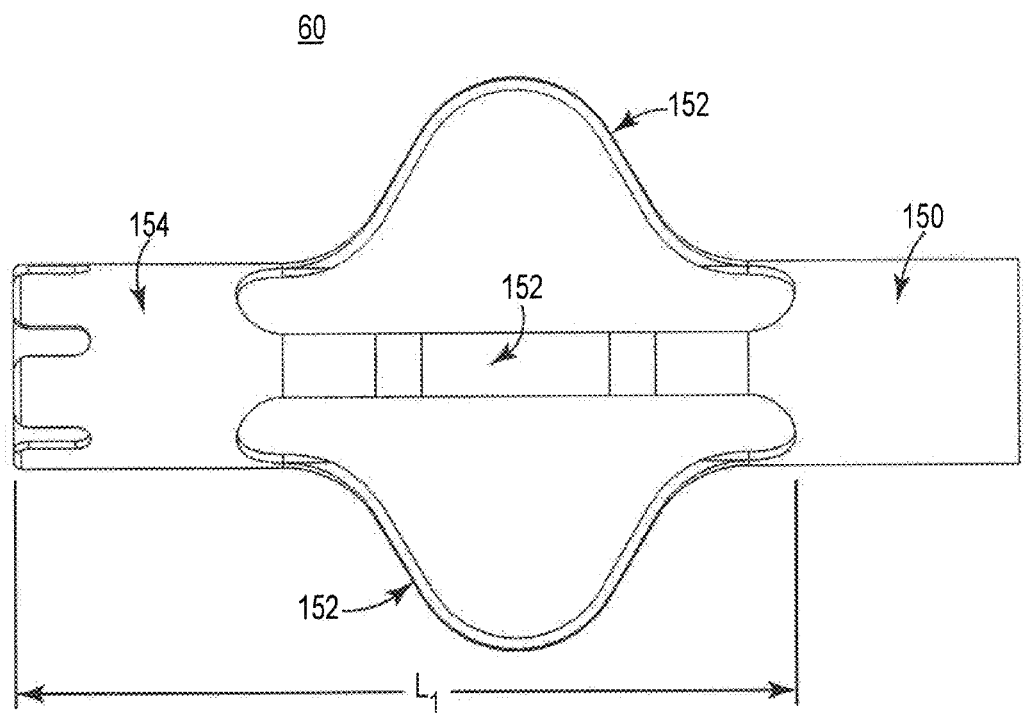
FIG. 6A is a simplified, side view of the release sheath assembly component of the delivery device of FIG. 3 and in a normal state.
Figure 6B:
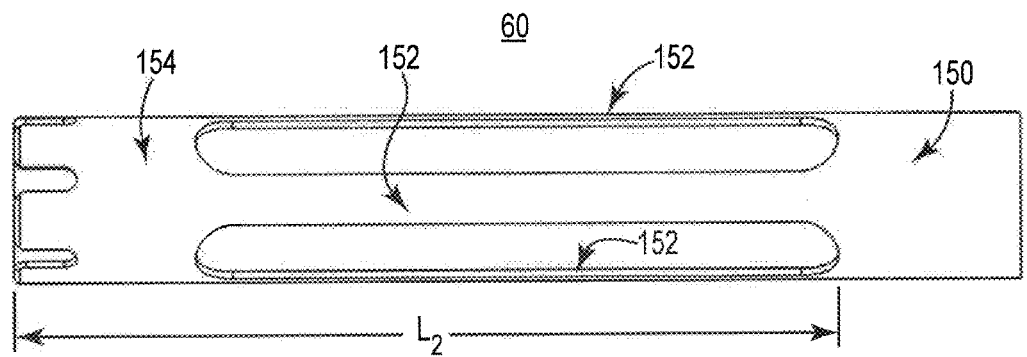
FIG. 6B is a simplified view of the release sheath assembly of FIG. 6A and in a compressed state.

Operation of the release sheath assembly 60 in facilitating partial and full deployment of a prosthetic heart valve is based upon a longitudinal position of the release sheath 154 as dictated by biasing members 152. As mentioned above, the biasing members 152 are formed to normally assume the curved shape generally reflected in FIG. 3. A diameter collectively defined by the biasing members 152 (in their normal state) is greater than a diameter of the delivery sheath assembly lumen 76. Thus, when the release sheath assembly 60 is disposed within the capsule 62 (or within the delivery sheath shaft 70), the biasing members 152 are forced to deflect radially inwardly, effectuating an increase in a longitudinal spacing between the collar 150 and the release sheath 154. Upon removal of this external force, the biasing members 152 self-revert back to the natural condition reflected in FIG. 3, thereby biasing the release sheath 154 to an original longitudinal spacing relative to the collar 150. FIGS. 6A and 6B illustrate this relationship in simplified form. FIG. 6A reflects a normal state of the biasing members 152 that establishes a first longitudinal spacing $L_1$ between the collar 150 and the release sheath 154. When subjected to a compressive force (e.g., upon insertion within the delivery sheath assembly 52 (FIG. 3)), the biasing members 152 deflect inwardly as shown in FIG. 6B. Because the collar 150 is spatially fixed (i.e., attached to the inner support shaft 80 (FIG. 3)), the deflected biasing members 152 force the release sheath 154 away from the collar 150, to a second longitudinal spacing $L_2$ that is greater than the first longitudinal spacing $L_1$. When the compressive force is removed, the biasing members 152 self-revert back to the arrangement of FIG. 6A, thereby pulling the release sheath 154 back toward the collar 150.

Returning the FIG. 3, the handle 58 generally includes a housing 170 and an actuator mechanism 172 (referenced generally). The housing 170 maintains the actuator mechanism 172, with the actuator mechanism 172 configured to facilitate sliding movement of the delivery sheath assembly 52 relative to the inner shaft assembly 54. The housing 170 can have any shape or size appropriate for convenient handling by a user. In one simplified construction, the actuator mechanism 172 includes a user interface or actuator 174 slidably retained by the housing 170 and coupled to a sheath connector body 176. The proximal end 72 of the delivery sheath assembly 52 is coupled to the sheath connector body 176 (e.g., via an optional mounting boss 178 in some embodiments). The inner shaft assembly 54, and in particular the proximal tube 86, is slidably received within a passage 180 of the sheath connector body 176, and is rigidly coupled to the housing 170. Sliding of the actuator 174 relative to the housing 170 thus causes the delivery sheath assembly 52 to move or slide relative to the inner shaft assembly 54, for example to effectuate deployment of a prosthesis from the inner shaft assembly 54 as described below. Alternatively, the actuator mechanism 172 can assume a variety of other forms differing from those implicated by the illustration of FIG. 3. Similarly, the handle 58 can incorporated other features, such as a cap 182 and/or a fluid port assembly 184.

Figure 7A:
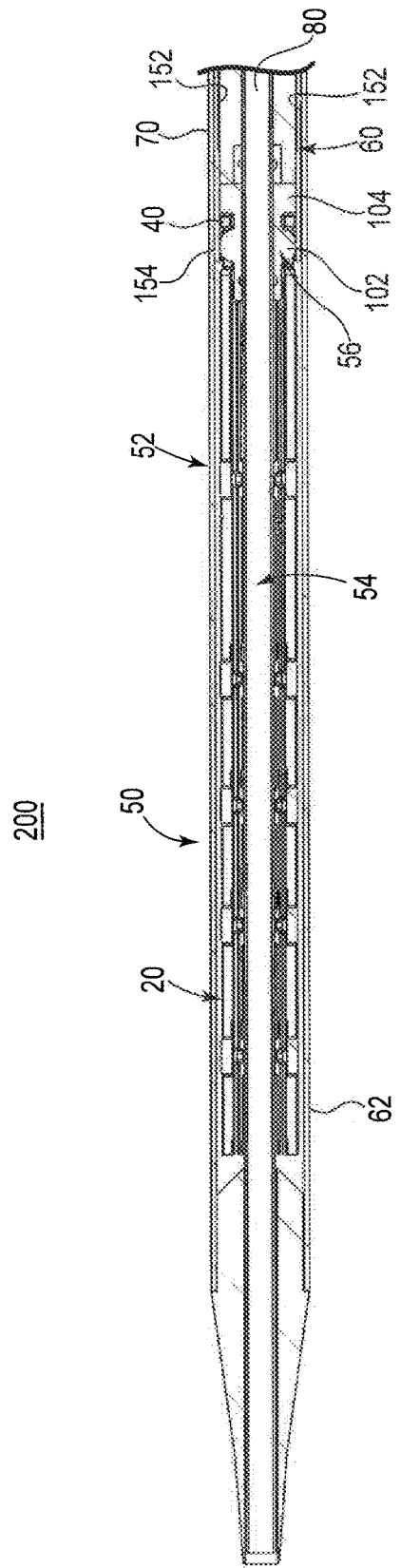
FIG. 7A is a cross-sectional view of a portion of a heart valve repair system in accordance with the present disclosure, including the delivery device of FIG. 3 loaded with the prosthetic heart valve of FIG. 1A.

FIG. 7A illustrates a portion of a system 200 in accordance with the present disclosure for repairing a defective heart valve of a patient and including the stented prosthetic heart valve 20 within the delivery system 50. In the loaded state of the delivery device 50 in FIG. 7A, the prosthetic heart valve 20 is crimped over the inner shaft assembly 54, with the delivery sheath assembly 52 located such that the capsule 62 surrounds and compressively retains the prosthetic heart valve 20 in the compressed arrangement shown thereby defining a loaded condition of the repair system 200. The spindle 56 and the release sheath assembly 60 (referenced generally) are mounted to the inner support shaft 80, with the release sheath 154 being slidably directed over the hub 102 via deflection of the biasing members 152 in response to placement within the delivery sheath shaft 70. The release sheath 154 can be slidably supported along the flange 104 to better ensure desired positioning relative to the hub 102. With this arrangement, then, the posts 40 of the prosthetic heart valve 20 are captured to the hub 102 via the release sheath 154.

Figure 7B:
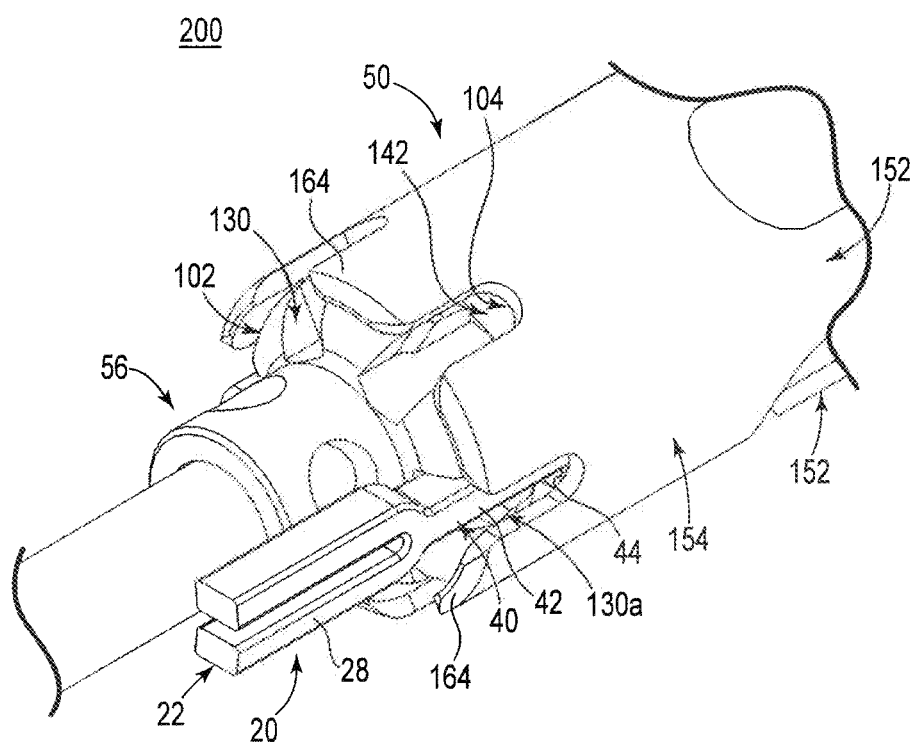
FIG. 7B is an enlarged, perspective view of a portion of the system of FIG. 7A.

Engagement of the prosthetic heart valve 20 with the spindle 56 is more fully illustrated in FIG. 7B. As a point of reference, FIG. 7B illustrates a portion of the delivery system 200 in the loaded condition including a portion of the delivery device 50 in the loaded state along with a portion of the prosthetic heart valve 20. For ease of explanation, the delivery sheath assembly 52 (FIG. 3) is omitted from the view of FIG. 7B, it being understood, however, that in the loaded state, the delivery sheath assembly 52 acts upon the biasing members 152 (shown partially in FIG. 7B), causing the release sheath 154 to slide distally over the flange 104 and a portion of the hub 102. Further, only one of the posts 40 (and corresponding wire segments 28) of the prosthetic heart valve stent frame 22 is shown in FIG. 7B, and is disposed within the first longitudinal slot 130a. It will be recognized that the stent frame 22 typically includes a plurality of the posts 40, individual ones of which are similarly received in respective ones of the remaining slots 130. With this in mind, in the loaded condition of FIG. 7B, the shoulder 42 of the post 40 slidably nests within the slot 130a, and the head 44 (primarily hidden in the view of FIG. 7B) nests within the trough 142. A radial height or thickness of the post 40 is less than a height of the slot 130a (and less than a radial height of the flange 104) such that the post 40 does not project radially beyond the slot 130a or the trough 142. It will be recalled that in some constructions, the stent frame 22 is configured to self-expand from the compressed arrangement reflected by FIG. 7B. While the capsule 62 (FIG. 3) serves to resist this expansion, the release sheath 154 further ensures robust retention of the post 40 with the hub 102. In particular, the fingers 164 of the release sheath 154 extend over the trough 142, and thus over a portion of the head 44. As a result, the head 44 is effectively captured within the trough 142 by the release sheath 154.

Figure 8A:
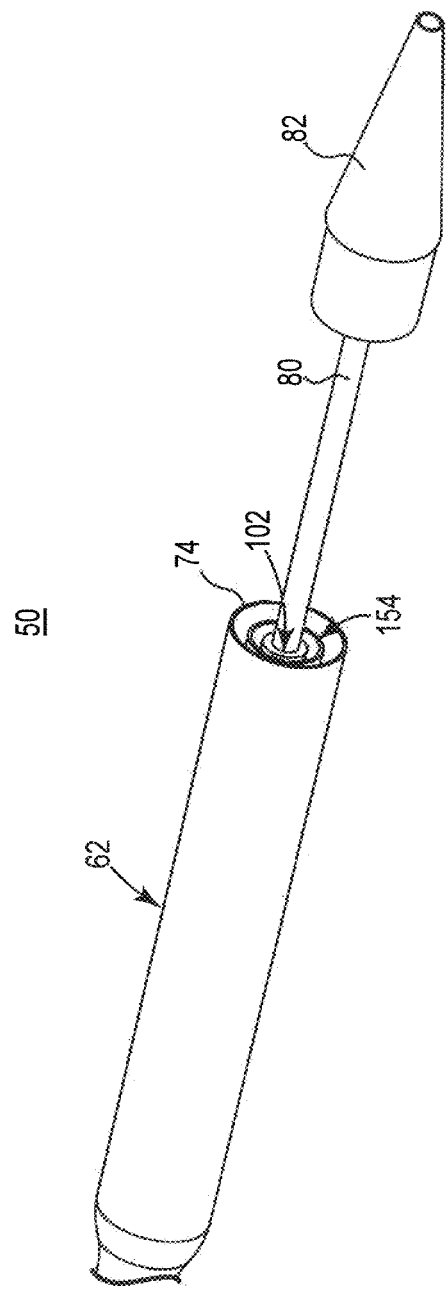
FIG. 8A is a perspective view of the delivery device of FIG. 3 in an initial stage of a partial deployment state.
Figure 8B:
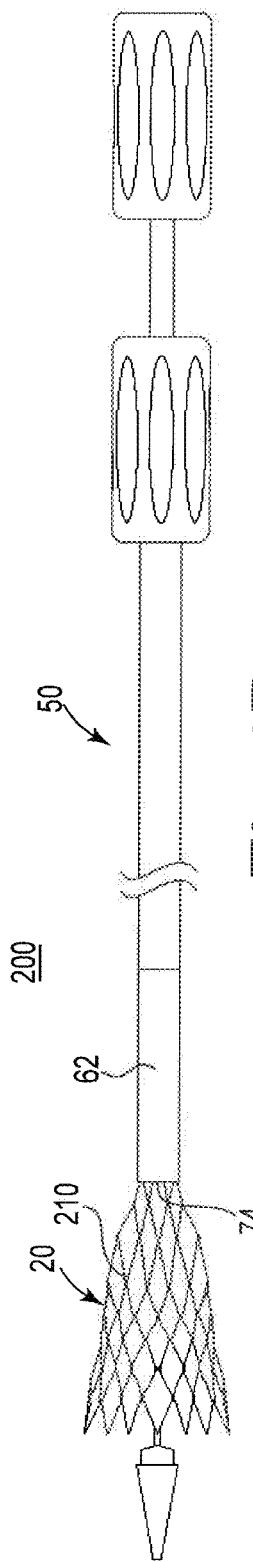
FIG. 8B is a simplified side view of the system of FIG. 7A in an initial stage of a deployment condition, includes the delivery device in the arrangement of FIG. 8A.

The loaded delivery system 200 can then be used to percutaneously deliver the prosthetic heart 20 valve to an implantation site, such as a defective heart valve. For example, the delivery device 50 is manipulated to advance the compressed prosthetic heart valve 20 toward the implantation site in a retrograde manner through a cut-down to the femoral artery, into the patient's descending aorta, over the aortic arch, through the ascending aorta, and approximately midway across the defective aortic valve (for an aortic valve repair procedure). The prosthetic heart valve 20 can then be partially or fully deployed from the delivery device 50. With either procedure, the capsule 62 (FIG. 3) is proximally retracted or withdrawn from over the prosthetic heart valve 20. As generally reflected in FIG. 8A, proximal retraction of the capsule 62 continues, with the distal end 74 being approximately over the hub 102. Because the biasing members 152 (FIG. 3) are still within the capsule 62 in the arrangement of FIG. 8A, the release sheath 154 remains in the distally forward position relative to the hub 102. For ease of illustration, the prosthetic heart valve 20 is not shown in the view of FIG. 8A. However, FIG. 8B illustrates, in simplified form, partial retraction of the capsule 62 and the resultant self-expansion of an exposed, distal region 210 of the prosthetic heart valve 20 relative to the distal end 74 of the capsule 62.

Figure 8C:
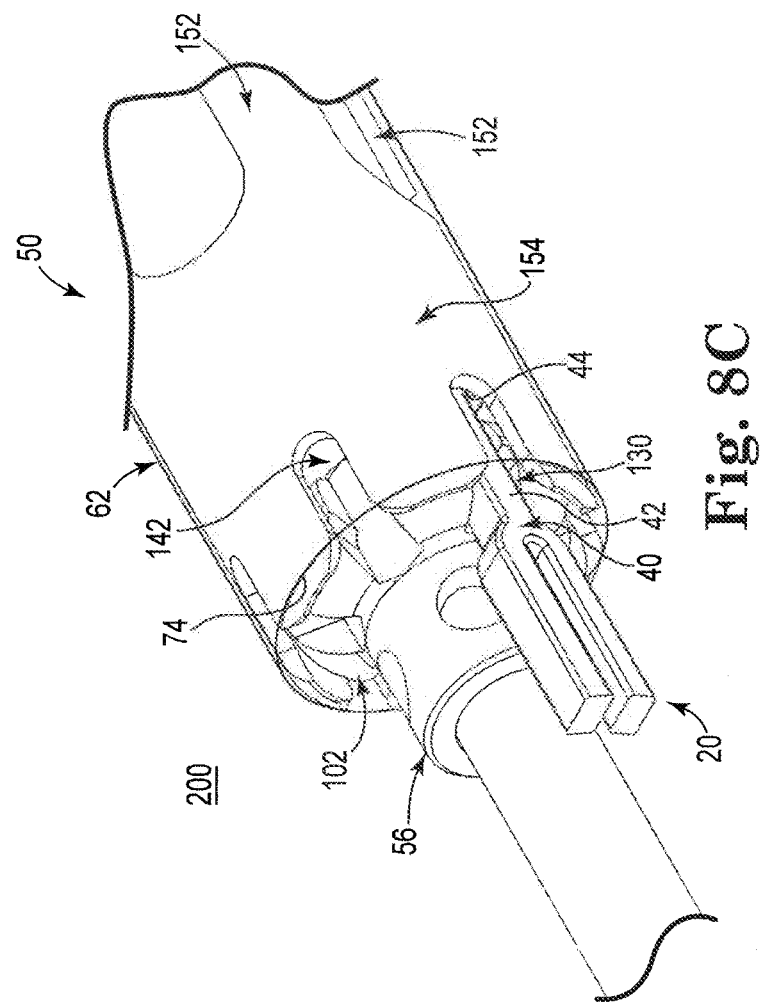
FIG. 8C is an enlarged, perspective view of a portion of the delivery system in the partial deployment stage of FIG. 8A.

With additional reference to FIG. 8C, so long as the distal end 74 of the capsule 62 (shown in phantom in FIG. 8C) is distal the biasing members 152, the biasing members 152 remain in a deflected condition such that the release sheath 154 remains over the hub 102. Thus, the shoulder 42 of each of the posts 40 (one of which is illustrated in FIG. 8C) remains captured within the corresponding slot 130 as described above, as does the head 44 (referenced generally) within the trough 142. As a result, in the stage of the partial deployment state of FIG. 8C, the prosthetic heart valve 20 is able to partially expand or deploy, yet remains coupled to the delivery device 50 (via the spindle 56 and the release sheath 154).

Figure 8D:
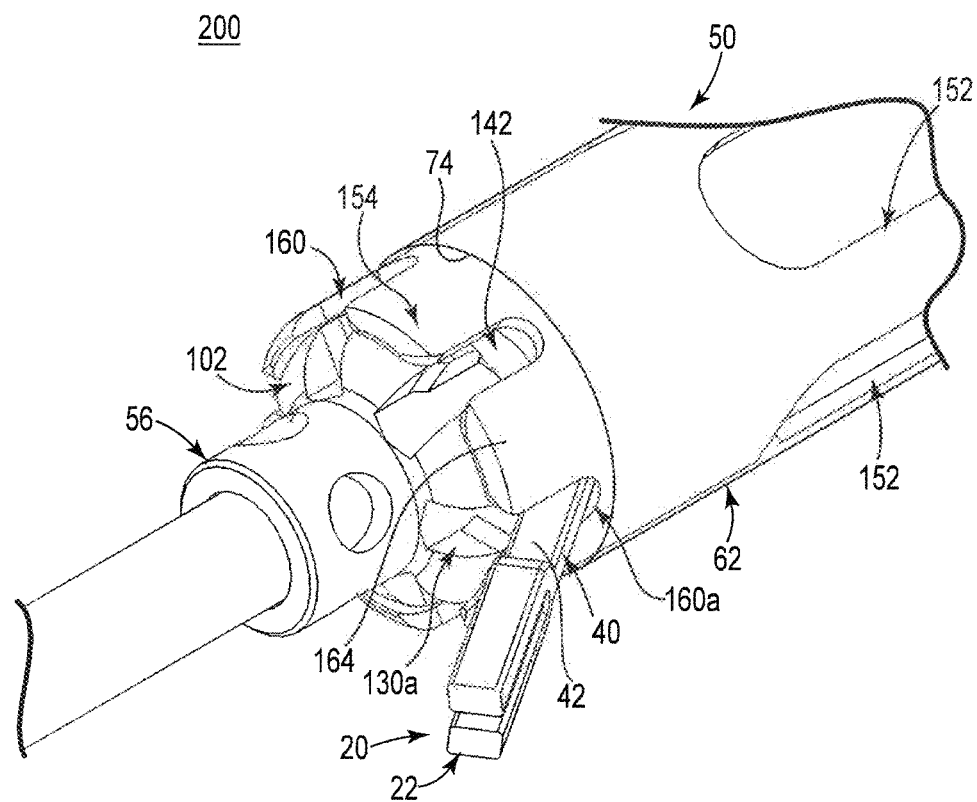
FIG. 8D is an enlarged, perspective view of the system of FIG. 7A in a further stage of the partial deployment state.

Partial deployment of the prosthetic heart valve 20 can also include further sequential retraction of the capsule 62 from the position of FIG. 8C. For example, in the partial deployment stage reflected in FIG. 8D, the distal end 74 of the capsule 62 (drawn in phantom) is further retracted relative to the hub 102 (as compared to the stage of FIG. 8C), with the distal end 74 located proximal the notches 160. However, because the biasing members 152 are still within, and thus acted upon by, the capsule 62, the release sheath 154 remains over the trough 142 such that the stent frame 22 is coupled to the spindle 56 (via the posts 40). With embodiments in which the release sheath 154 forms the notches 160, FIG. 8D further reflects that in this stage of the partial deployment state, the stent frame post 40 can pivot relative to the spindle 56. More particularly, with respect to the first slot 130a within which the post 40 of FIG. 8D is disposed, the corresponding first notch 160a of the release sheath 154 is longitudinally aligned with the first slot 130a. Thus, with the distal end 74 of the capsule 62 proximal the first notch 160a, the self-expanding attribute of the stent frame 22 causes the shoulder 42 of the post 40 to slide through the first slot 130a and the first notch 160a, with the head 44 effectively pivoting within the trough 142. Even with this pivoting movement, the head 44 (hidden in the view of FIG. 8D, but shown, for example, in FIG. 2) remains captured within the trough 142 via the fingers 164.

In the stage of partial deployment of FIG. 8D (or in any other sequentially prior stage of partial deployment), the clinician can perform desired evaluations of the partially deployed prosthetic heart valve 20 relative to the implantation site. Notably, a substantial majority of the prosthetic heart valve 20 is in an expanded arrangement, including, for example, the inflow region 30 (FIG. 1A) and at least a portion of the outflow region 32 (FIG. 1A). Thus, the repair systems and delivery devices and methods of the present disclosure afford the clinician the ability to make an accurate estimate of the position of the prosthetic heart valve 20 relative to the implantation site. Under circumstances where the clinician determines that the prosthetic heart valve 20 should be repositioned, the capsule 60 can, in some constructions, be distally advanced back over the prosthetic heart valve 20, thereby resheathing or recapturing the prosthetic heart valve 20 and returning to the compressed arrangement. Alternatively, the delivery device 50 can incorporate other features to effectuate recapturing of the prosthetic heart valve 20.

Figure 9A:
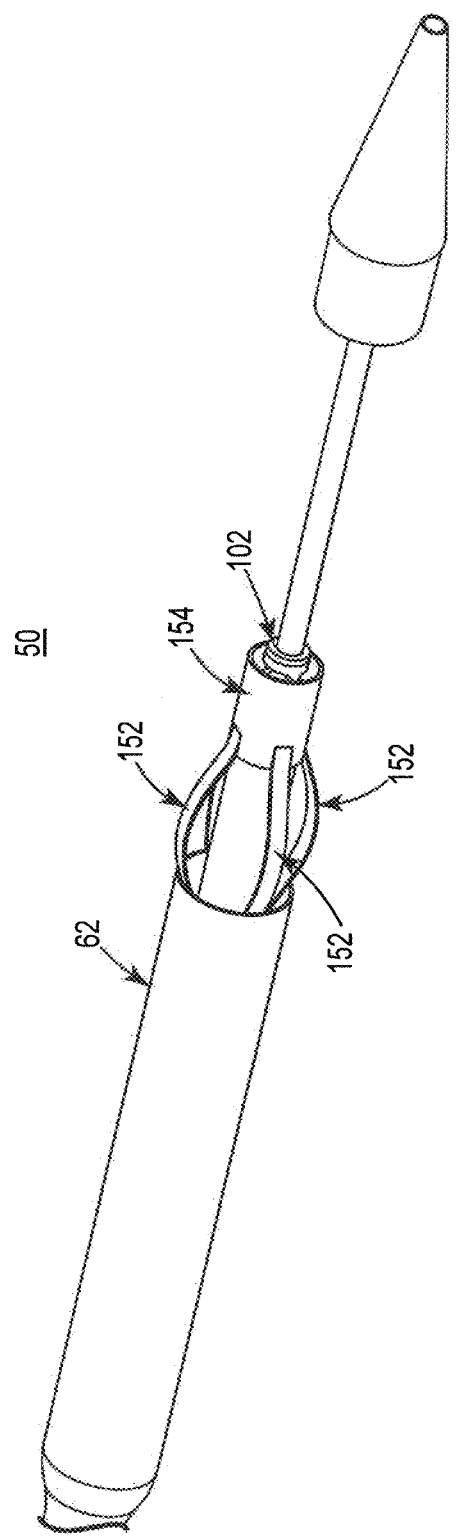
FIGS. 9A and 9B are simplified perspective views of the delivery device of FIG. 3 in various stages of transitioning to a deployment state.
Figure 9B:
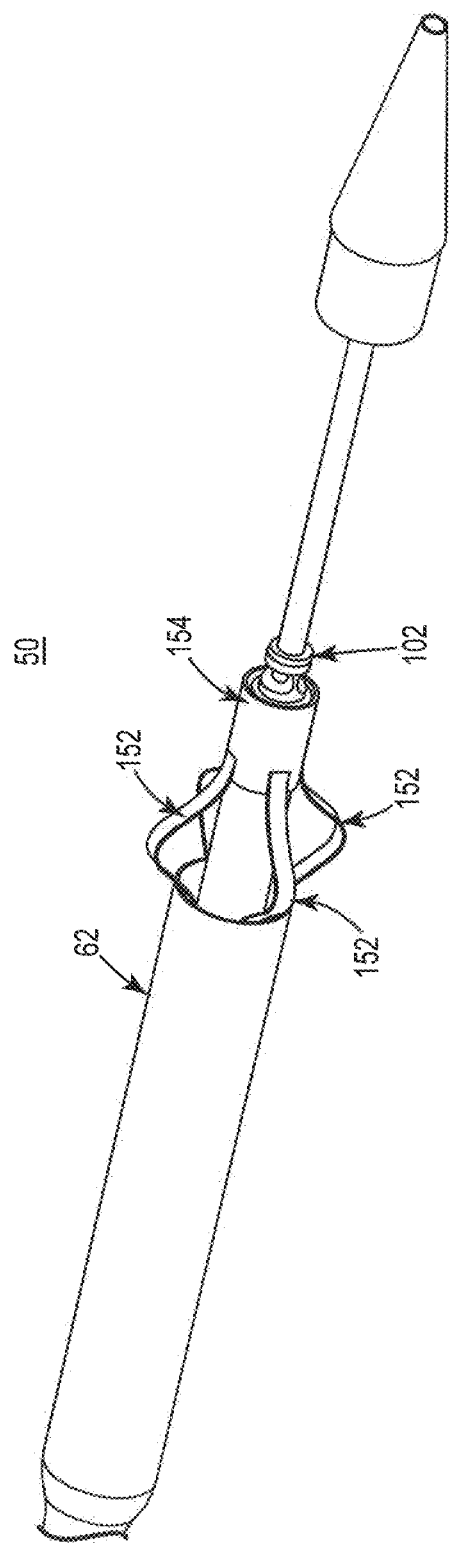

When full deployment of the prosthetic heart valve 20 from the delivery device 50 is desired, the capsule 62 is further proximally retracted over the biasing members 152. As shown in FIGS. 9A and 9B (the prosthesis 20 (FIG. 1A) being omitted from the views of FIGS. 9A and 9B for ease of explanation), as the biasing members 152 are sequentially released from the confines of the capsule 62, the biasing members 152 self-revert toward their natural state. This action, in turn, causes the biasing members 152 to proximally retract the release sheath 154 from the hub 102 as reflected by a comparison of the arrangement of FIG. 9A with that of FIG. 9B.

Figure 10A:
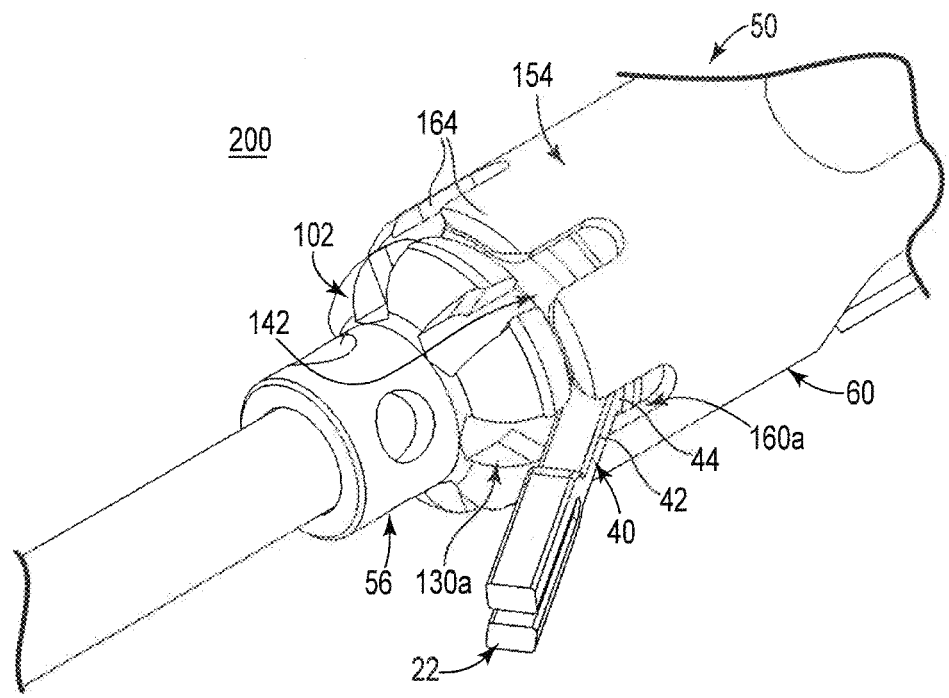
FIGS. 10A and 10B are enlarged, perspective views of a portion of the delivery system of FIG. 7A and illustrating transitioning to a deployment condition in which the a prosthetic heart valve deploys from the delivery device.
Figure 10B:
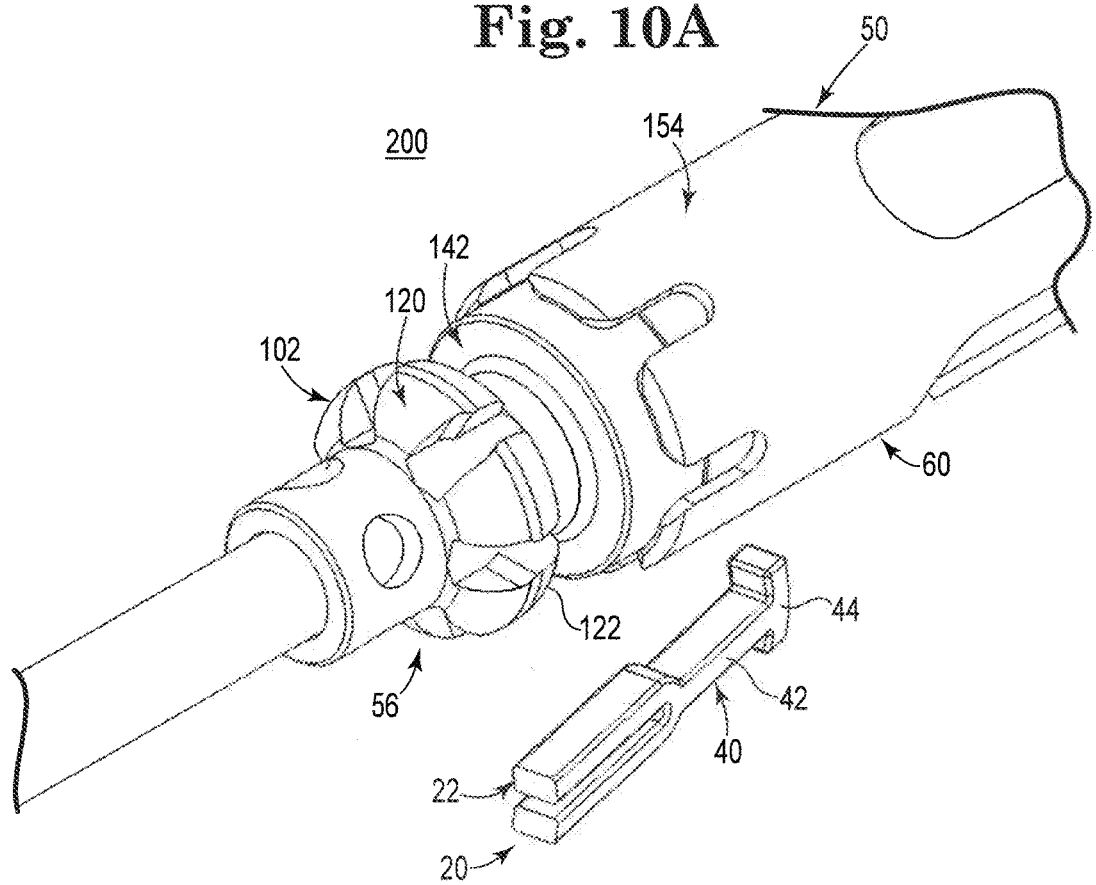

Retraction of the release sheath 154 from the hub 102 permits the stent posts 40 to fully release from the spindle 56 as shown in FIGS. 10A and 10B. For example, in the view of FIG. 10A, the release sheath 154 has partially retracted from the hub 102, with the fingers 164 projecting across at least a portion of the trough 142. This arrangement permits the posts 40 (one of which is illustrated in FIGS. 10A and 10B) to further pivot relative to the spindle 56 (e.g., the head 44 pivots within the tough 142), with the shoulder 42 extending outwardly through the corresponding first slot 130a and first notch 160a. Upon complete retraction of the release sheath 154 proximally beyond the trough 142, the head 44 is no longer captured by the release sheath 154, and thus fully releases from the spindle 56 (due to self-expansion of the prosthetic heart valve stent frame 22) as shown in FIG. 10B. In this regard, the head 44 only minimally contacts or interfaces with the outer surface 120 of the hub 102 in releasing from the spindle 56. To the extent any such contact occurs, it will be along the proximal segment 122 of the hub outer surface 120. Because the proximal segment 122 is curved and free of sharp edges or corners, the head 44 interfaces or easily slides along the curved proximal segment 122. The head 44 will not "catch" on the spindle 56 when fully releasing from the delivery device 50. Thus, the posts 40 consistently release from the spindle 56.

While the delivery device 50 has been described as incorporating the release sheath assembly 60, in other embodiments, the release sheath assembly 60 can have differing forms or can be omitted. For example, alternative delivery device configurations capture the prosthetic heart valve stent frame 22 relative to the spindle 56 via the delivery sheath assembly 52 (FIG. 3) alone. With these constructions, full deployment of the prosthetic heart valve 20 is effectuated once the distal end 74 (FIG. 3) of the capsule 62 (FIG. 3) is proximal the trough 142.

The delivery devices of the present disclosure provide percutaneous placement of a stented prosthetic heart valve for replacement of an aortic valve, for example. Alternatively, the systems and devices can be used for replacement of other valves and/or in other portions of the body in which a stent is to be implanted. When delivering a valved stent to replace an aortic valve, the delivery devices of the present disclosure can be used with a retrograde delivery approach, for example, although it is contemplated that an antegrade delivery approach can be used, with certain modifications to the delivery device. With the repair systems described herein, full or partial blood flow through the native valve can advantageously be maintained during a period when the valved stent is being deployed into the patient, but is not yet released from its delivery device. This feature can help to prevent complications that may occur when blood flow is stopped or blocked during valve implantation with some other known delivery devices. In addition, it is possible for the clinician to thereby evaluate the opening and closing of leaflets, examine for any paravalvular leakage, and evaluate coronary flow and proper positioning of the prosthetic heart valve within the target anatomy before final release of the stented prosthesis.

The delivery devices shown and described herein can be modified for delivery of balloon-expandable stented prosthetic heart valves, within the scope of the present disclosure. That is to say, delivering balloon-expandable stents to an implantation location can be performed percutaneously using modified versions of the delivery devices of the present disclosure. In general terms, this includes providing a transcatheter assembly that can include a delivery sheath and/or additional sheaths as described above. The devices will further include a delivery catheter, a balloon catheter, and/or a guide wire. A delivery catheter used in this type of delivery device defines a lumen within which the balloon catheter is received. The balloon catheter, in turn, defines a lumen within which the guide wire is slidably disposed. Further, the balloon catheter includes a balloon that is fluidly connected to an inflation source. With the stented valve mounted to the balloon, the transcatheter assembly is delivered through a percutaneous opening in the patient via the delivery device. Once the stented prosthetic heart valve is properly positioned, the balloon catheter is operated to inflate the balloon, thus transitioning the stented prosthesis to an expanded arrangement.

The systems, devices, and methods of the present disclosure provide a marked improvement over previous designs. The delivery device is configured so that the stent frame of the stented prosthetic heart valve will release from the delivery device at a pre-designated step of the delivery sequence. This delivery device thereby advantageously allows the clinician to entirely remove an outer sheath from a valved stent prior to releasing the stent from the delivery device. In addition, the repair systems of the present disclosure allow the inflow region and at least a portion of the outflow region of the valved stent to open or release so that the valve structure function can be determined prior to final release of the stented valve. The disclosed spindle provides a simplified design that does not have any edges on which the stent frame of the prosthetic heart valve might otherwise "catch", thereby ensuring desired deployment, as well as promoting use with the T-like shaped posts of the prosthetic heart valve stent frame to permit open assessment prior to full deployment.

Although the present disclosure has been described with reference to preferred embodiments, workers skilled in the art will recognize that changes can be made in form and detail without departing from the spirit and scope of the present disclosure.

What is claimed is:

1. A delivery device for percutaneously deploying a stented prosthetic heart valve including a stent frame to which a valve structure is attached, the device comprising:
   a delivery sheath assembly terminating at a distal end and defining a lumen;
   an inner shaft slidably disposed within the lumen; and
   a spindle attached to the shaft, the spindle including:
   a tubular base,
   a hub projecting radially outwardly relative to the base, wherein:
   the hub defines at least one longitudinal slot sized to slidably receive a corresponding post of a prosthetic heart valve stent frame, wherein the at least one longitudinal slot is defined by opposing side walls and a floor, and further wherein the tubular base includes a ring immediately proximal the hub, the ring having a surface aligned with the floor,
   an outer surface of the hub forms a proximal segment and a distal segment, the proximal segment being curved in extension toward the distal segment and defining a ramp-like face immediately adjacent the base, the distal segment defining a distal face, wherein the at least one longitudinal slot is open at the proximal and distal faces;
   wherein the device is configured to provide a loaded state in which the delivery sheath assembly retains a stented prosthetic heart valve over the inner shaft and coupled to the spindle via the at least one slot, and a deployment state in which the distal end of the delivery sheath assembly is withdrawn from the prosthetic heart valve to permit the prosthetic heart valve to release from the at least one longitudinal slot.

2. The delivery device of claim 1, wherein the at least one longitudinal slot includes a plurality of circumferentially spaced longitudinal slots formed in the hub.

3. The delivery device of claim 2, wherein the plurality of longitudinal slots are equidistantly spaced from one another about a circumference of the hub.

4. The delivery device of claim 1, wherein the spindle further includes a flange projecting radially outwardly relative to the base and proximally spaced from the hub by the ring.

5. The delivery device of claim 4, wherein an outer diameter of the flange approximates a maximum outer diameter of the hub.

6. The delivery device of claim 1, wherein the outer surface defines a convex curve in longitudinal extension along the proximal segment.

7. The delivery device of claim 1, wherein the outer surface, as collectively defined by the proximal and distal segments, approximates a semi-circle in longitudinal extension.

8. The delivery device of claim 1, further comprising:
a release sheath assembly disposed between the delivery sheath assembly and the spindle in the loaded state, the release sheath assembly including a release sheath slidably received over at least the proximal segment of the hub in the loaded state.

9. The delivery device of claim 8, wherein the release sheath assembly is configured to proximally retract the release sheath relative to the hub with proximal retraction of the delivery sheath distal end from the release sheath.

10. The delivery device of claim 8, wherein the release sheath forms at least one longitudinal notch extending from a distal end of the release sheath, and further wherein upon final assembly in the loaded state, the at least one notch is longitudinally aligned with the at least one slot.

11. The delivery device of claim 10, wherein the at least one longitudinal slot includes a plurality of circumferentially spaced longitudinal slots, and the at least one notch includes a plurality of circumferentially spaced notches, and further wherein each of the slots is longitudinally aligned with a respective one of the notches.

12. The delivery device of claim 11, wherein the spindle further forms a circumferential trough between the hub and a flange formed proximal the hub, and further wherein the release sheath includes a plurality of fingers spaced from one another by the plurality of notches, and further wherein the loaded state includes the fingers extending across the circumferential trough.

13. A system for repairing a defective heart valve of a patient, the system comprising:
a prosthetic heart valve having a stent frame and a valve structure attached to the stent frame, the stent frame defining a distal region and a proximal region, the proximal region forming at least one post; and
a delivery device comprising:
a delivery sheath assembly terminating at a distal end and defining a lumen,
an inner shaft slidably disposed within the lumen,
a spindle attached to the inner shaft, the spindle including:
a tubular base,
a hub projecting radially outwardly relative to the base and defining at least one longitudinal slot sized to slidably receive the at least one post, wherein the outer surface of the hub forms a proximal segment and a distal segment, the proximal segment being curvilinear to define a convex curve in extension toward the distal segment and a ramp-like proximal face in extension toward the base, the distal segment defining a distal face, wherein the at least one longitudinal slot is open at the proximal and distal faces;
wherein the system is configured to provide a loaded condition in which the prosthetic heart valve is retained between the delivery sheath assembly and the inner shaft, including the at least one post slidably captured within the at least one longitudinal slot.

14. The system of claim 13, wherein the at least one longitudinal slot includes a plurality of circumferentially spaced longitudinal slots, and further wherein the at least one post includes a plurality of posts corresponding with the plurality of longitudinal slots.

15. The system of claim 13, wherein the spindle further includes a flange projecting radially outwardly relative to the base and proximally spaced from the hub to define a circumferential trough.

16. The system of claim 15, wherein the at least one post includes a distal shoulder and a proximal head, the shoulder sized to slidably nest within the longitudinal slot and the head sized to slidably nest within the trough.

17. The system of claim 16, wherein a circumferential width of the head is larger than a circumferential width of the shoulder.

18. The system of claim 17, wherein the shoulder and the head collectively define a T-like shape.

19. The system of claim 13, wherein the system is further configured to provide a deployment condition in which the distal end of the delivery sheath assembly is proximal the hub to permit the at least one post to release from the at least one slot, including a head of the at least one post sliding along the curved proximal segment of the hub outer surface.

20. The system of claim 19, wherein the stent frame is configured to radially self-expand from a compressed arrangement to a normal arrangement, and further wherein the loaded condition includes the delivery sheath assembly compressively retaining the prosthetic heart valve in the compressed arrangement.

21. The system of claim 20, wherein the deployment condition includes the stent frame self-expanding to the normal arrangement.

22. The system of claim 13, wherein the delivery device further includes:
a release sheath assembly disposed between the delivery sheath assembly and the spindle in the loaded state, the release sheath assembly including a release sheath slidably received over at least the proximal segment of the hub in the loaded state.

23. The system of claim 22, wherein the release sheath forms at least one longitudinal notch extending from a distal end of the release sheath, and further wherein upon final assembly in the loaded condition, the at least one notch is longitudinally aligned with the at least one slot.

24. The system of claim 23, wherein the system is further configured to provide a deployment condition, including the release sheath proximally retracted from the hub and the at least one post self-pivoting through the at least one slot and the at least one notch.

25. The system of claim 24, wherein the at least one post includes a distal shoulder and a proximal head, and further wherein the spindle forms a circumferential trough proximal the hub such that the loaded condition includes the shoulder disposed within the at least one slot and the head disposed within the trough, the head being releasably captured within the trough by the release sheath.

26. A method of percutaneously deploying a stented prosthetic heart valve to an implantation site of a patient, the method comprising:
receiving a delivery device loaded with a radially expandable prosthetic heart valve having a stent frame to which a valve structure is attached, the delivery device including a delivery sheath assembly containing the prosthetic heart valve in a compressed arrangement over an inner shaft in a loaded state of the device, and a spindle attached to the shaft, the spindle including:
a tubular base,
a hub projecting radially outwardly relative to the base and defining at least one longitudinal slot and an outer surface forming a proximal segment and a distal segment, the proximal segment being curved in extension toward the distal segment and defining a ramp-like proximal face immediately adjacent the base, the distal segment defining a distal face, wherein the at least one longitudinal slot is open at the proximal and distal faces,
wherein a post of the stent frame is slidably captured within the at least one longitudinal slot in the loaded state;
delivering the prosthetic heart valve in the compressed arrangement through a bodily lumen of the patient and to the implantation site via the delivery device in the loaded state;
proximally retracting the delivery sheath assembly from the prosthetic heart valve; and
permitting the post to release from the at least one longitudinal slot, including a surface of the post sliding along the curved proximal segment of the hub outer surface such that the prosthetic heart valve deploys from the delivery device.

27. The method of claim 26, wherein the at least one longitudinal slot includes a plurality of circumferentially spaced longitudinal slots, and further wherein the post includes a plurality of posts corresponding with the plurality of longitudinal slots.

28. The method of claim 26, wherein the stent frame is configured to radially self-expand from a compressed arrangement to a normal arrangement, and further wherein the loaded state includes the delivery sheath assembly compressively retaining the prosthetic heart valve in the compressed arrangement.

29. The method of claim 26, wherein the delivery device further includes:
a release sheath assembly disposed between the delivery sheath assembly and the spindle in the loaded state, the release sheath assembly including a release sheath slidably received over at least the proximal segment of the hub.

30. The method of claim 29, wherein the release sheath forms at least one longitudinal notch extending from a distal end of the release sheath, and further wherein permitting the post to release from the at least one longitudinal slot includes the post pivoting relative to the spindle such that a portion of the post moves through the at least one longitudinal slot and a corresponding one of the at least one notch.

* * * * *